US012631205B2

(12) United States Patent
Teschke

(10) Patent No.: US 12,631,205 B2
(45) Date of Patent: May 19, 2026

(54) FIXATION DEVICE FOR SURGICAL INSTRUMENT PARTS

(71) Applicant: Stryker European Operations Limited, Carrigtwohill (IE)

(72) Inventor: Dieter Teschke, Merdingen (DE)

(73) Assignee: Stryker European Operations Limited, Carrigtwohill (IE)

( * ) Notice: Subject to any disclaimer, the term of this patent is extended or adjusted under 35 U.S.C. 154(b) by 460 days.

(21) Appl. No.: 18/110,198

(22) Filed: Feb. 15, 2023

(65) Prior Publication Data

US 2023/0255723 A1     Aug. 17, 2023

(30) Foreign Application Priority Data

Feb. 16, 2022    (EP) ..................................... 22157032

(51) Int. Cl.
*F16B 7/18*          (2006.01)
*A61B 17/00*         (2006.01)
(Continued)

(52) U.S. Cl.
CPC ................ *F16B 7/182* (2013.01); *F16B 7/02* (2013.01); *A61B 2017/00486* (2013.01); (Continued)

(58) Field of Classification Search
CPC ........... A61B 90/57; A61B 2017/0046; A61B 2017/00477; A61B 2017/00486; (Continued)

(56) References Cited

U.S. PATENT DOCUMENTS 370,168 A  *   9/1887   Truxal  .................... F16D 1/096
                                                        403/344
738,445 A  *   9/1903   Hoffman  ................ F16D 1/096
                                                        403/371
(Continued)

FOREIGN PATENT DOCUMENTS

DE        202007003957 U1     7/2008
DE        202012100091 U1 *   2/2012    ............ F16B 7/0486
(Continued)

OTHER PUBLICATIONS

Machine-assisted English translation for DE 20 2007 003 957 U1 extracted from the espacenet.com database on Feb. 16, 2023, 14 pages.
(Continued)

*Primary Examiner* — Josh Skroupa
(74) *Attorney, Agent, or Firm* — Howard & Howard Attorneys PLLC

(57)          ABSTRACT

A fixation device for fixing a first part of a surgical instrument to a second part of the surgical instrument. The fixation device has a longitudinal axis and includes a fixation body configured to accommodate a portion of the first instrument part and a portion of the second instrument part therein. A first fastening member and at least one movable first clamping member are configured to clampingly engage at least the first instrument part so as to fix at least the first instrument part to the fixation device. A first actuation member is configured to receive at least a portion of the fixation body. The first actuation member includes a second fastening member configured to engage with the first fastening member. The first actuation member is configured to exert a clamping force on the first clamping member when the second fastening member is in engagement with the first fastening member.

15 Claims, 12 Drawing Sheets

(51) Int. Cl.
    *A61B 34/20*     (2016.01)
    *F16B 7/02*     (2006.01)

(52) U.S. Cl.
    CPC ................. *A61B 2034/2051* (2016.02); *A61B 2034/2072* (2016.02); *Y10T 403/7069* (2015.01)

(58) Field of Classification Search
    CPC ........ B23B 31/2012; F16B 7/02; F16B 7/025; F16B 7/048; F16B 7/149; F16B 7/18; F16B 7/182; F16D 1/093; F16D 1/094; Y10T 403/5761; Y10T 403/5766; Y10T 403/5786; Y10T 403/5793; Y10T 403/68; Y10T 403/69; Y10T 403/7056; Y10T 403/7058; Y10T 403/7069; Y10T 403/76
    USPC ....... 403/309, 310, 313, 314, 343, 344, 370, 403/371, 374.4, 409.1
    See application file for complete search history.

(56) References Cited

U.S. PATENT DOCUMENTS

| | | | | |
|---|---|---|---|---|
| 1,631,250 A | * | 6/1927 | Daniel, Sr. ................ | F16B 7/02 403/308 |
| 3,003,149 A | * | 10/1961 | Grashow .............. | H01Q 1/1207 403/371 |
| 3,751,027 A | | 8/1973 | Giles | |
| 4,757,778 A | * | 7/1988 | Scaglia ................... | F16B 7/149 403/109.5 |
| 5,649,780 A | * | 7/1997 | Schall ...................... | B25G 1/04 403/370 |
| 5,695,297 A | * | 12/1997 | Geib ....................... | F16B 7/149 403/371 |
| 6,712,544 B2 | * | 3/2004 | Kruger .................. | F16B 5/0233 403/370 |
| 7,270,349 B2 | | 9/2007 | Bamberger et al. | |
| 2005/0031424 A1 | | 2/2005 | Hernandez et al. | |
| 2012/0083794 A1 | | 4/2012 | Martin et al. | |
| 2012/0259353 A1 | | 10/2012 | Houser et al. | |
| 2015/0182293 A1 | | 7/2015 | Yang et al. | |
| 2020/0157819 A1 | * | 5/2020 | Lee ......................... | F16B 7/182 |

FOREIGN PATENT DOCUMENTS

| | | | | |
|---|---|---|---|---|
| DE | 102014100362 A1 | 7/2015 | | |
| EP | 1564419 A2 | * 8/2005 | ............. | F16B 9/054 |
| EP | 2777522 A1 | 9/2014 | | |
| WO | 03044416 A1 | 5/2003 | | |
| WO | 2006076962 A2 | 7/2006 | | |

OTHER PUBLICATIONS

Machine-assisted English language abstract and machine-assisted English language translation for DE 10 2014 100 362 A1 extracted from espacenet.com database on Feb. 16, 2023, 24 pages.
English language abstract for WO U.S. Appl. No. 03/044,416 A1 extracted from espacenet.com database on Feb. 16, 2023,2 pages.
English language abstract and machine-assisted English translation for WO 2006/076962 A2 extracted from espacenet.com database on Feb. 16, 2023, 12 pages.

* cited by examiner

600

610 Accommodate a portion of a first instrument part and a portion of a second instrument part in a fixation body of a fixation device 620 Fasten a fastening member of an actuation member to a fastening member of the fixation body for fixing the first and second instrument parts to the fixation device

FIXATION DEVICE FOR SURGICAL INSTRUMENT PARTS

PRIORITY CLAIM

This application claims priority under 35 U.S.C. § 119 to European Patent Application No. 22157032.8, filed Feb. 16, 2022, the entire contents of which are hereby incorporated by reference.

TECHNICAL FIELD

The present disclosure generally relates to the field of surgical instruments. In particular, a fixation device for fixing a first part of a surgical instrument to a second part of the surgical instrument is presented. Also presented are a system comprising the fixation device and the surgical instrument as well as a method of using the fixation device.

BACKGROUND

Various surgical tracking and navigation techniques are used for assisting a surgeon or for controlling operation of a surgical robot. In some navigation variants, medical image data of a patient are visualized on a display and overlaid with a model, position or trajectory of a handheld surgical instrument tracked by a tracking system. In other variants, a tracked robot arm with a surgical instrument is navigated relative to the patient.

In such tracking and navigating techniques, trackers are commonly attached to a patient anatomy and to the surgical instrument. The relative position between the patient anatomy and a surgical instrument are determined and, for example, visualized or used for robot control.

In the fields of surgical tracking and navigation, it is mandatory that tracking and navigation operations are performed at a high degree of accuracy, since any inaccuracy may result in harming the patient. It is mandatory to not only accurately determine a position of the tracked surgical instrument but to know the exact geometry of the surgical instrument. In particular, the geometric relation between the tracker attached to the surgical instrument and a tip of the surgical instrument has to be known at all times.

Common surgical instruments are designed to be usable for multiple different tasks, e.g., by utilizing a replaceable tip analogous to a common drilling machine or multifunctional tool. Such surgical instruments often comprise multiple instrument parts that can detachably be fixed to each other. For example, a first instrument part may be configured to transfer mechanical or electric energy to a detachable second instrument part that carries a surgical instrument tip. Evidently, each mechanical connection is subject to mechanical play. Due to such mechanical play between instrument parts, the geometric relation between a tracker attached to a first part of the surgical instrument and the instrument tip carried by, or constituting, the other part of the surgical instrument can only be determined in the order of accuracy of the mechanical play. As such, the accuracy of surgical tracking and navigation is negatively impacted if such mechanical play is present.

Of course, there exist further reasons to reduce mechanical play between two parts of a surgical instrument. In some cases, the first instrument part serves as a grip or handle for the surgeon while the second, replaceable instrument part comprises a tip for performing or assisting a surgical procedure. Any mechanical play between the two instrument parts will negatively impact the precision at which the surgical procedure can be carried out.

SUMMARY

There is a need to reduce a mechanical play between two parts of a surgical instrument.

According to a first aspect, a fixation device for fixing a first part of a surgical instrument to a second part of the surgical instrument is provided. The fixation device has a longitudinal axis and comprises a fixation body configured to accommodate a portion of the first instrument part and a portion of the second instrument part therein. The fixation body comprises a first fastening member and at least one movable first clamping member configured to clampingly engage at least the first instrument part so as to fix at least the first instrument part to the fixation device. The fixation device further comprises a first actuation member configured to receive at least a portion of the fixation body. The first actuation member comprises a second fastening member configured to engage with the first fastening member. The first actuation member is configured to exert a clamping force on the first clamping member when the second fastening member is in engagement with the first fastening member.

According to one variant, at least one of the fixation body and the first actuation member may have a structural configuration such that the clamping force is adjustable by a relative movement between the fixation body and the first actuation member along the longitudinal axis. The structural configuration may define a shape of at least one of the first fastening member, the first clamping member, the first actuation member and the second fastening member. For example, the structural configuration may comprise a region that is inclined relative to the longitudinal axis. In some variants, multiple such inclined regions may be provided, possibly at different but cooperating components. The inclined regions may thus be configured to cooperate with each other. For example, a first inclined region at the fixation device (e.g., at a location where the first fastening member or the first clamping member is present) cooperates with a second inclined region at the first actuation member (e.g., at a location where the second fastening member is present).

In some variants, the inclined region may comprise at least one planar or non-planar surface. At least a part of the inclined region may be inclined at an angle between 2 degrees and 15 degrees relative to the longitudinal axis, e.g., between 5 degrees and 10 degrees, such as at an angle of approximately 7 degrees.

The inclined region may extend circumferentially about at least a portion of the longitudinal axis. In case the inclined region fully extends circumferentially about the longitudinal axis, the inclined region may, for example, define a cone or a pyramidal frustum extending along the longitudinal axis. The cone or pyramidal frustum may be coaxial to the longitudinal axis.

The structural configuration may comprise a protrusion extending substantially perpendicular (e.g., towards or away from) the longitudinal axis. The protrusion may extend circumferentially about at least a portion of the longitudinal axis. In some variants, there may be multiple protrusions. For example, at least one of the first actuation member and the first clamping member may each comprise at least one protrusion.

Due to the structural configuration, the clamping force exerted on the first clamping member may depend on the relative position between the fixation body and the first actuation member along the longitudinal axis. For example, moving the fixation body and the first actuation member towards each other may increase the clamping force, and vice versa.

According to one variant, the fixation body may have a slot extending along a length thereof. The slot may enable an adaptable cross-section of the fixation body perpendicular to the longitudinal axis of the fixation body. The cross-section may be adaptable to the size of at least one of the first and second instrument parts to be accommodated by the fixation body.

The fixation body may be a single piece. The fixation body may have a tubular shape, i.e., may comprise an outer surface facing away from the longitudinal axis and an inner surface facing the longitudinal axis. The cross-sectional shape of the fixation body may be defined by the shape of the outer surface and the inner surface. For example, the cross-section of at least one of the outer surface and the inner surface may be circular, elliptic, rectangular or polygonal.

The first actuation member may be configured as a sleeve. The first actuation member may be formed as a single piece. The first actuation member may be rigid. An inner surface of the first actuation member may be shaped to conform to the outer surface of the fixation body, i.e., circular, elliptic, rectangular or polygonal.

One, two or more (e.g., three to ten) first clamping members may be provided. The at least one first clamping member may be a clamping finger configured to be deformed towards the longitudinal axis when the clamping force is exerted thereon. In case of multiple movable first clamping members (e.g., multiple clamping fingers), the first clamping members may be located spaced apart from each other circumferentially around the longitudinal axis. The first clamping members may be located symmetrically around the longitudinal axis. Each of the first clamping members may have a surface facing the longitudinal axis and being shaped based on the shape of at least the first instrument part to be fixed to the fixation device.

The first fastening member and the second fastening member may be configured to releasably engage each other. The first fastening member and the second fastening member may be configured as complementary threads. The complementary threads may be located on the inclined region or spaced apart therefrom. At least one thread parameter (e.g., at least one of a type, size, pitch and tap tolerance) of the complementary threads may be selected based on at least one of the angle at which the inclined region is inclined relative to the longitudinal axis and a play between the fixation body and at least one of the first and second instrument parts when the fixation body is not engaged by the actuation member, i.e., between the unclamped fixation body and at least one of the first and second instrument parts. For example, the pitch of the complementary threads may be at least 0.1 mm, e.g., at least 0.25 mm. The pitch may in some implementations be less than 2 mm or less than 1 mm. The complementary threads may be configured in a self-locking manner.

Additionally or alternatively, the first fastening member and the second fastening member may comprise complementary snap fit components. Of course, other components capable of engagement, in particular a form-fitting engagement, can be used as well.

According to one variant, the fixation body may comprise an alignment member configured to align the fixation body with at least one of the first instrument part and the second instrument part in a circumferential direction relative to the longitudinal axis. The alignment member of the fixation body may be configured to cooperate with a complementary alignment member of at least one of the two instrument parts. The alignment member may be a groove or a protrusion. The alignment member may be located on a fixation body surface facing the longitudinal axis.

In some implementations, the fixation body may have a third fastening member and at least one movable second clamping member configured to clampingly engage at least the second instrument part so as to fix at least the second instrument part to the fixation device. The fixation device may further comprise a second actuation member. The second actuation member may be configured to receive at least a portion of the fixation body and may comprise a fourth fastening member. The second actuation member may be configured to exert a clamping force on the second clamping member when the fourth fastening member is in engagement with the third fastening member.

The second actuation member may structurally be similar, or identical, to the first actuation member. The fixation body may have two opposing ends along its longitudinal extension. The first fastening member may be located adjacent one end of the fixation body, and the third fastening member may be located adjacent another end of the fixation body. The second clamping member may structurally be similar, or identical, to the first clamping member.

According to a second aspect, a method for fixing two parts of a surgical instrument to each other using a fixation device having a longitudinal axis is provided. The fixation device comprises a fixation body configured to accommodate a portion of the first instrument part and a portion of the second instrument part therein. The fixation body comprises a first fastening member and at least one movable first clamping member configured to clampingly engage at least the first instrument part so as to fix at least the first instrument part to the fixation device. The fixation device further comprises a first actuation member configured to receive at least a portion of the fixation body. The first actuation member comprises a second fastening member configured to engage with the first fastening member. The first actuation member is configured to exert a clamping force on the first clamping member when the second fastening member is in engagement with the first fastening member. The method comprises accommodating a portion of the first instrument part and a portion of the second instrument part in the fixation body and fastening the second fastening member of the first actuation member to the first fastening member of the fixation body for fixing at least the first instrument part to the fixation device.

According to one variant, the fixation body may have a third fastening member and at least one movable second clamping member configured to clampingly engage at least the second instrument part so as to fix at least the second instrument part to the fixation device. The fixation device may further comprise a second actuation member configured to receive at least a portion of the fixation body. The second actuation member may comprise a fourth fastening member. The second actuation member may be configured to exert a clamping force on the second clamping member when the fourth fastening member is in engagement with the third fastening member. The method may further comprise fastening the fourth fastening member of the second actuation member to the third fastening member of the fixation body for fixing at least the second instrument part to the fixation device.

According to a third aspect, a fixation system is provided. The fixation system comprises a surgical instrument having a first instrument part and a second instrument part. The fixation system further comprises the fixation device as presented herein.

According to one variant, the first instrument part may be configured to transfer mechanical or electrical energy to the second instrument part. The first instrument part may be configured as a grip or handle. The first instrument part may accommodate a battery. The first instrument part may belong to an arm of a surgical robot.

The second instrument part may accommodate a motor powered by a battery in the first instrument part or by a power cord. The second instrument part may comprise a mechanically or electrically operable instrument tip. The instrument tip may be operable by the motor or may be energized by the battery or a power cord. The instrument tip may be (e.g., detachably) attached to the second instrument part or may constitute the second instrument part. The instrument tip may be a tip configured for a surgical procedure, e.g., for drilling, cutting or burring. In other implementations, the instrument tip may be configured to apply an electrical voltage or ultrasound to tissue.

The fixation system may further comprise a tracker attachable or attached to the first instrument part. The tracker may be a tracker for surgical navigation, e.g., an optical or electromagnetic tracker. The fixation device for fixing the first instrument part with the second instrument part may be configured to reduce mechanical play between the first instrument part and the second instrument part (e.g., so as to enable reliably determining the position of the second instrument part, or a portion thereof, based on a tracked position of the first instrument part).

BRIEF DESCRIPTION OF THE DRAWINGS

Further features and advantages of the fixation device, the system and the method presented herein are described below with reference to the accompanying drawings, in which.

DETAILED DESCRIPTION

Figure 1:
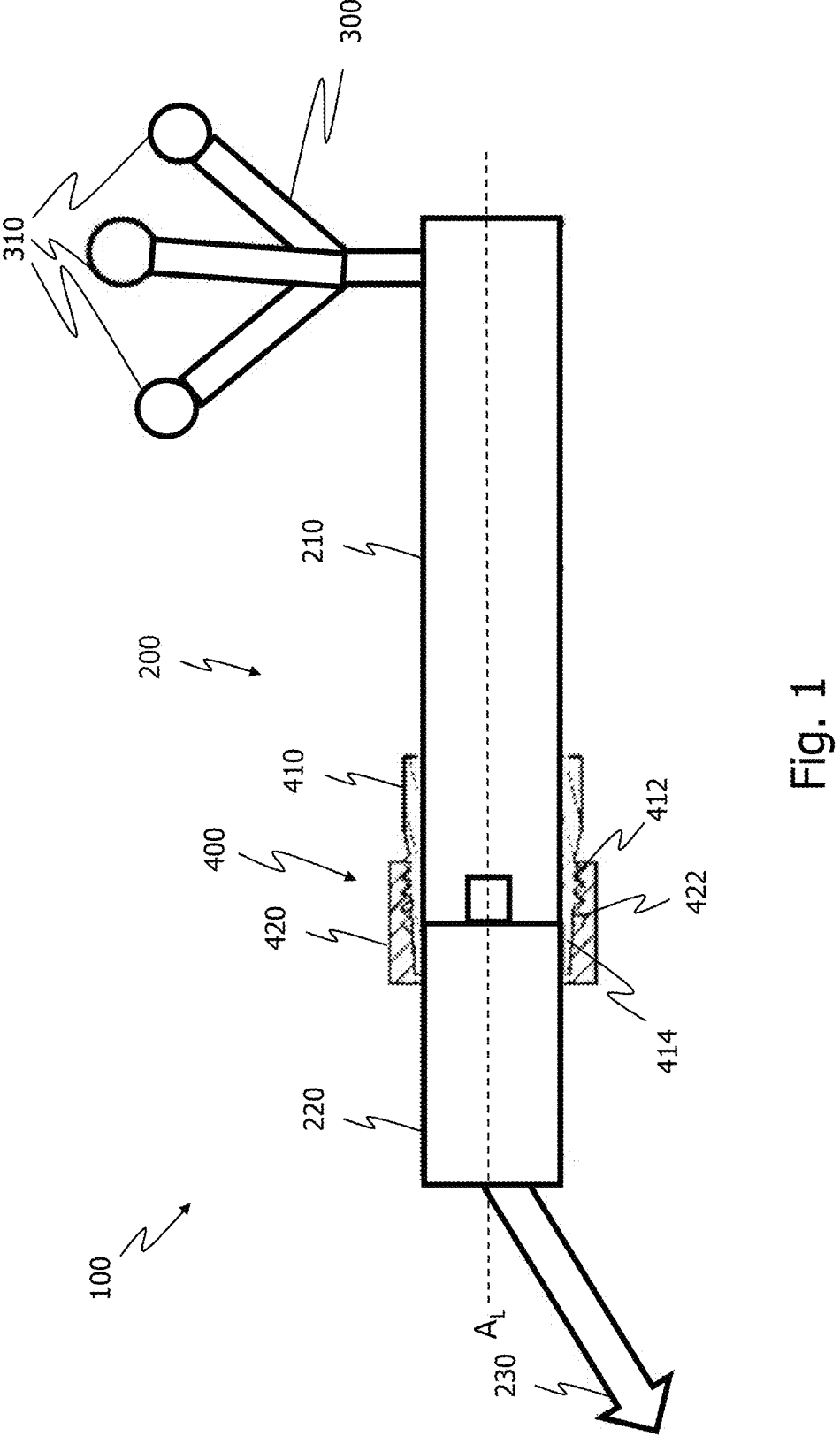
FIG. 1 illustrates a schematic representation of a fixation system comprising a surgical instrument, a fixation device and a tracker.

In the following description, for purposes of explanation and not limitation, specific details are set forth in order to provide a thorough understanding of the present disclosure. It will be apparent to one skilled in the art that the present disclosure may be practiced in other embodiments that depart from these specific details.

The same reference numerals are used to denote the same or similar components.

FIG. 1 illustrates a schematic representation of a first embodiment of a fixation system 100. The fixation system 100 comprises a surgical instrument 200 with a first part 210 and a second part 220. In the present embodiment, the first and second instrument parts 210, 220 have substantially cylindrical shapes of arbitrary cross section. The first and second instrument parts 210, 220 are detachably connected to each other (e.g., via a plug-type connection, quick-release connection, tool-holder connection or otherwise). The connection may generally be realized as a form-fitting connection or a frictional connection. Additionally, or in the alternative, the connection may be configured so that a torque can be transmitted between the two instrument parts 210, 220. In some variants, the connection may not, or not fully, reduce a mechanical play between the two instrument parts 210, 220.

The surgical instrument 200 may be a powered surgical instrument. In such a case, the first instrument part 210 may accommodate a battery and the second instrument part 220 may accommodate a motor electrically powered by the battery. In some variants, the motor can alternatively be accommodated in the first instrument part 210. The second instrument part 220 further comprises an instrument tip 230. The instrument tip 230 may be mechanically powered by the motor. The instrument tip 230 may be a drill, a burr or a saw blade.

In other variants, the surgical instrument 200 may be a non-powered surgical instrument, like a screw driver having a first instrument part 210 configured as a grip or handle and a second instrument part 220 with an instrument tip 230 configured as a screw driver blade. The first and second instrument parts 210, 220 may be connected (e.g., in a form-fitting manner but with a certain mechanical play) such that torque can be transmitted from the grip or handle to the screw driver blade.

The fixation system 100 further comprises a tracker 300 detachably attached to the first instrument part 210. The tracker 300 is a common optical tracker 300 comprising three (or more) markers 310 trackable, e.g., by a camera of a surgical navigation system (not shown). The markers 310 may be active components (e.g., light emitting diodes, LEDs) or passive components (e.g., reflective spheres).

The fixation system 100 further comprises a fixation device 400 with a longitudinal axis $A_L$. The fixation device 400 is configured to fix the first instrument part 210 to the second instrument part 220. The fixation device 400 is a separate component that can be handled independently (and, e.g., removed) from the first and second instrument parts 210, 220.

The fixation device 400 is in some variants configured to reduce or prevent a mechanical play between the first and second instrument parts 210, 220. In such or other variants, the fixation device 400 may prevent the first and second instrument parts 210, 220 from being separable from each other. As such, the fixation device 400 can be used to maintain a geometric relationship between the instrument tip 230 of the second instrument part 210 and the tracker 300 attached to the first instrument part 220.

With continued reference to FIG. 1, the fixation device 400 comprises a tubular fixation body 410 accommodating a portion of the first instrument part 210 and a portion of the second instrument part 220. The fixation body 410 has a fastening member 412 located on an outer surface of the fixation body 410 facing away from the longitudinal axis A$_L$. In the present embodiment, the fastening member 412 is configured as a thread having a certain pitch of, for example, 0.25 mm. Moreover, the fixation body comprises movable clamping members 414 in clamping contact with both the first and second instrument parts 210, 220.

The fixation device 400 further comprises a tubular actuation member 420 that is similar to, e.g., a union nut. The actuation member 420 is a rigid, sleeve-like component and configured to receive a portion of the fixation body 410. In particular, the actuation member 420 is configured to receive the portion of the fixation body 410 comprising the movable clamping members 414 and the first fastening member 412. The actuation member 420 comprises a fastening member 422 (i.e., a thread complementary to the thread of the fastening member 412) located on an inner surface of the actuation member 420 facing the longitudinal axis A$_L$. The fastening member 422 is configured to engage with first fastening member 412 when the actuation member 420 receives the portion of the fixation body 410, as shown in FIG. 1. Evidently, other fastening members capable of (e.g., form-fittingly) engaging each other could be implemented as well.

A more detailed description of the fixation device 400 is given below with reference to FIGS. 2 to 4B.

Figures 2, 3A, 3B:
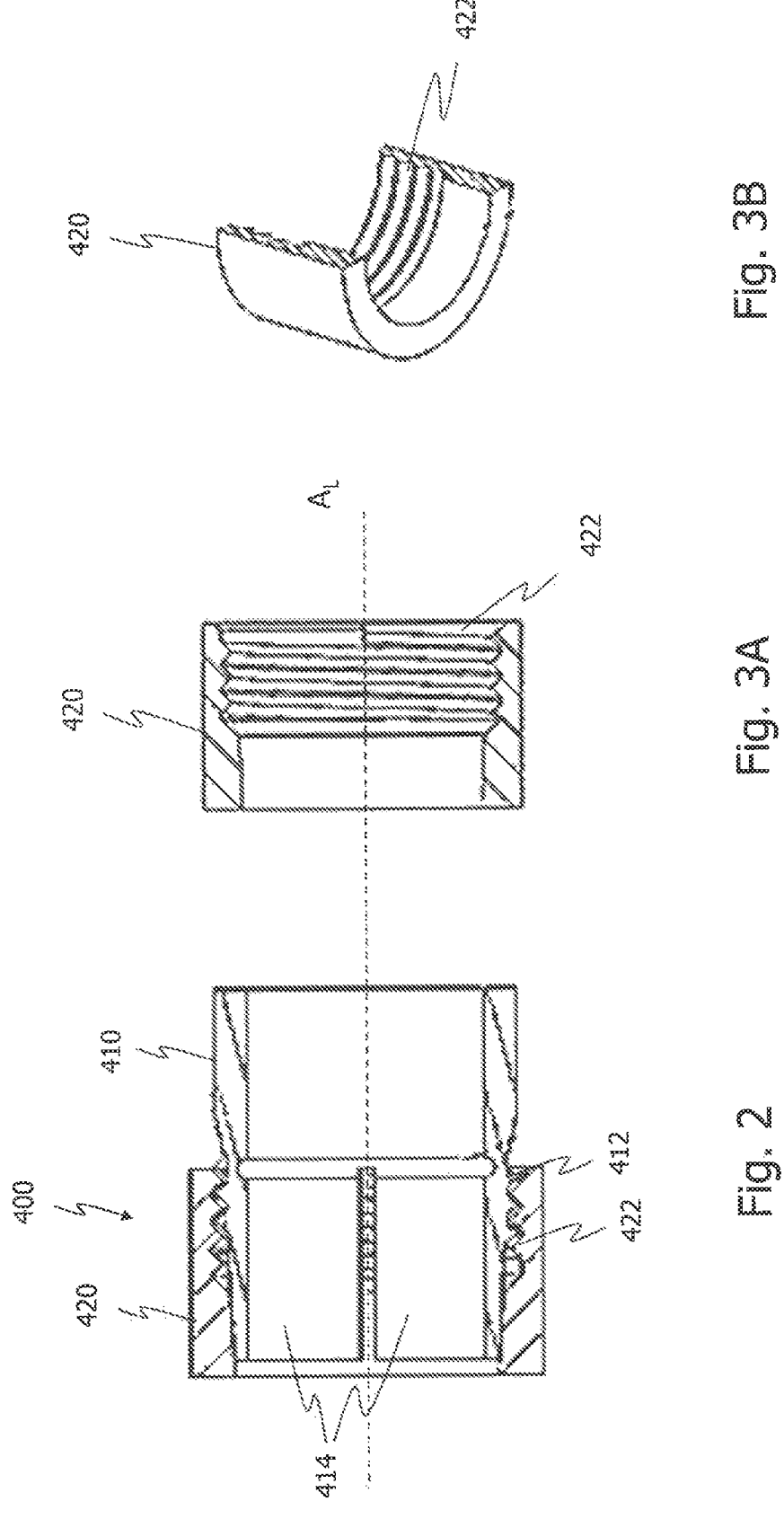
FIG. 2 illustrates a schematic representation of the fixation device shown in FIG. 1.
FIGS. 3A&3B illustrate schematic representations of an actuation member of the fixation device shown in FIG. 2.

FIG. 2 illustrates a cross-section of the fixation device 400 shown in FIG. 1 in more detail. The fixation device 400 is shown with the fixation body 410 and the actuation member 420 in an engaging configuration.

As shown in FIG. 2, the individual clamping members 414 of the fixation body 410 are separated via longitudinal slots extending parallel to the longitudinal axis A$_L$. The longitudinal slots separate the clamping members 414 to form individual clamping fingers 414 and enable the clamping members 414 to be movable towards the longitudinal axis A$_L$. The radially outer surface of the clamping members 414 has an inclined structural configuration (i.e., extends obliquely relative to the longitudinal axis A$_L$) and thus defines a radially outer conical portion. The radially outer surface of the clamping members 414 may be inclined at an angle between 2 degrees and 15 degrees relative to the longitudinal axis, e.g., at 7 degrees. The radially inner surface of the fixation body 410 has a cylindrical structural configuration (i.e., extends parallel to the longitudinal axis A$_L$).

Further, the radially inner surface of the actuation member 420 is inclined relative to the longitudinal axis A$_L$. The radially inner surface of the actuation member 420 may be inclined at an angle between 2 degrees and 15 degrees relative to the longitudinal axis, e.g., at 7 degrees. The radially inner surface thus defines a radially inner conical portion which is complementary to the radially outer conical portion of the fixation body 410. The inner diameter of the actuation member 420 therefore changes along a length thereof. In particular, the inner diameter of the actuation member 420 tapers in a receiving direction, i.e., in the direction in which at least a portion of the fixation body 410 is received by the actuation member 420. As a result of the tapering inner diameter of the actuation member 420, the movable members 414 are forced, or deflected, towards the longitudinal axis A$_L$ when the fixation body 410 is partially received within the actuation member 420.

In other words, the actuation member 420 is, due to its structural configuration, configured to exert a clamping force on the clamping members 414 when, as illustrated in FIG. 2, the fastening member 422 of the actuation member 420 is in engagement with the fastening member 412 of the fixation body 410. The engagement of the fastening members 412, 422 will therefore maintain the clamping force.

The clamping force exerted on the claiming members 414 is directed towards the longitudinal axis A$_L$, i.e., towards the portions of the first and second instrument parts 210, 220 accommodated within the fixation body 410. The magnitude of the exerted clamping force is dependent on the relative position between the fixation body 410 and the actuation member 420 along the longitudinal axis A$_L$ and, thus, on the length of engagement between fastening members 412, 422. Due to the exerted clamping force, the first and second instrument parts 210, 220 are fixed to the fixation device 400 and also to each other. As a result, mechanical play between the first and second instrument parts 210, 220 is reduced and the two instruments parts 210, 220 are prevented from separating from each other.

FIGS. 3A and 3B illustrate schematic representations of the actuation member 420 of the fixation device 400 shown in FIG. 2. FIG. 3A illustrates the fastening member 422, i.e., the thread, without the fixation body 410 being received in the actuation member 420. As shown in FIG. 3A, the thread tapers in accordance with the inclination of the radially inner surface of the actuation member 420. FIG. 3B illustrates a cut-out part of the actuation member 420 in a perspective view.

Figures 4A, 4B, 4C:
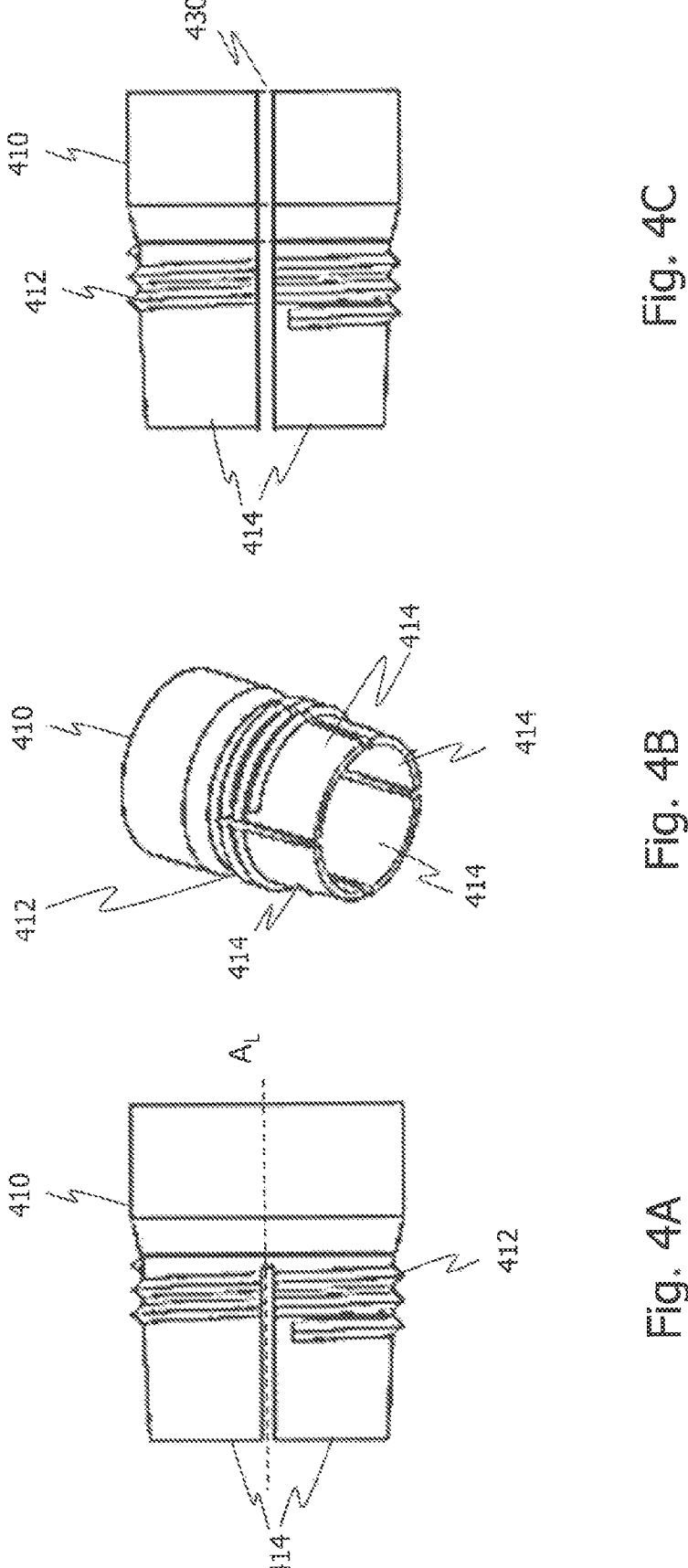
FIGS. 4A&4B illustrate schematic representations of a fixation body of the fixation device shown in FIG. 2.
FIG. 4C illustrates a schematic representation of another fixation body comprising a slot along a length thereof.

FIGS. 4A and 4B illustrate schematic representations of the fixation body 410 of the fixation device 400 shown in FIG. 2. FIG. 4A illustrates the fastening member 412, i.e., the thread, which is provided in a central portion of the fixation body 410 along the longitudinal axis A$_L$. FIG. 4B illustrates the fixation body 410 in a perspective view. As can be gathered from FIG. 4B, the fixation body 410 comprises four finger-like clamping members 414 separated by slots. The four clamping members 414 are located circumferentially about the longitudinal axis A$_L$ with each clamping member 414 having the same size (i.e., length and width). As a result, the clamping force is exerted homogenously.

Of course, the number of clamping members 414 can be selected as needed. In some variants, a single clamping member 414 may suffice, whereas in other variants two, three or more than four clamping members 414 may be beneficial. In the scenario of FIG. 4 The circumferential extension of a particular clamping member 414 about the longitudinal axis A$_L$ is approximately 90° in the scenario of FIG. 4B. The circumferential extension may generally range between 30° and 100°.

FIG. 4C illustrates a schematic representation of another fixation body 410 comprising four clamping members 414 with one separating slot 430 extending along the entire length thereof. The full-length slot 430 enables an adaptation of the fixation body 410, i.e., its cross-sectional size, perpendicular to the length of the fixation body. The cross-section of the fixation body 410 thus adapts itself to the cross-sectional size of at least one of the first and second instrument parts 210, 220 accommodated by the fixation body 410. In this embodiment, the fixation body 410 is made of a material that is elastically deformable.

Figures 5A, 5B:
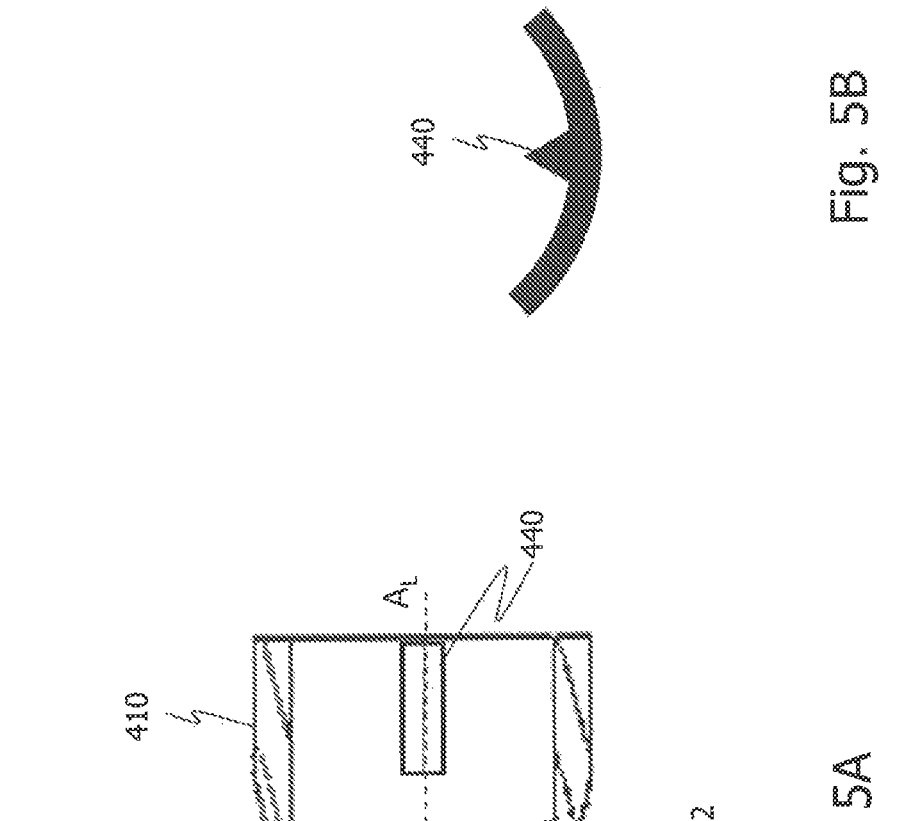
FIG. 5A illustrates a schematic representation of a fixation device comprising a fixation body with an alignment member.
FIG. 5B illustrates a schematic representation of a part of a cross-section of the fixation body of FIG. 5A.

FIG. 5A illustrates a schematic representation of a fixation device 400 similar to the fixation device 400 shown in FIG. 2. The fixation device 400 shown in FIG. 5A differs from the fixation device 400 shown in FIG. 2 in having a fixation body 410 that further comprises an alignment member 440. A cross-section of a part of the fixation body 410 of FIG. 5A at the position of the alignment member 440 is shown in FIG. 5B. The alignment member 440 shown in FIGS. 5A and 5B is a protrusion extending from the radially inner surface of the fixation body 410 towards the longitudinal axis $A_L$. The protrusion is configured to engage, for example, a corresponding groove or indentation (not shown) extending along at least a portion of at least one of the first and second instrument parts 210, 220. As a result, the alignment member 440 is configured to circumferentially align the fixation body 410 with at least one of the first and second instrument parts 210, 220. Aligning the fixation body 410 circumferentially with at least one of the first and second instrument parts 210, 220 facilitates fastening the second fastening member 422 of the actuation member 420 to the first fastening member 412 of the fixation body 410. Of course, the alignment member 440 could alternatively be a groove or indentation, with a mating protrusion being provided at one or both to the first and second instrument parts 210, 220.

Figure 6C:
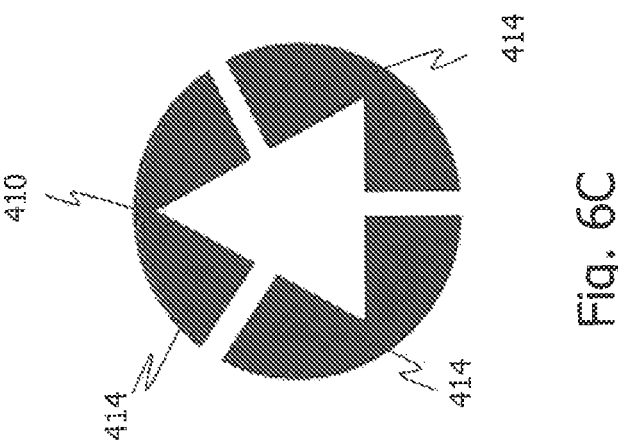
FIGS. 6A-6C illustrate schematic representations of cross-sections of different fixation bodies.
Figure 6B:
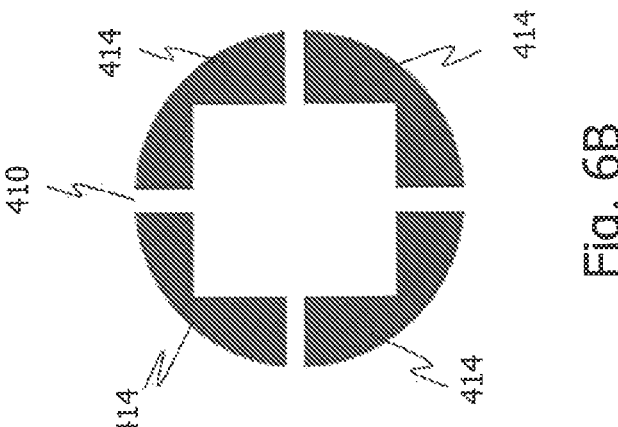
Figure 6A:
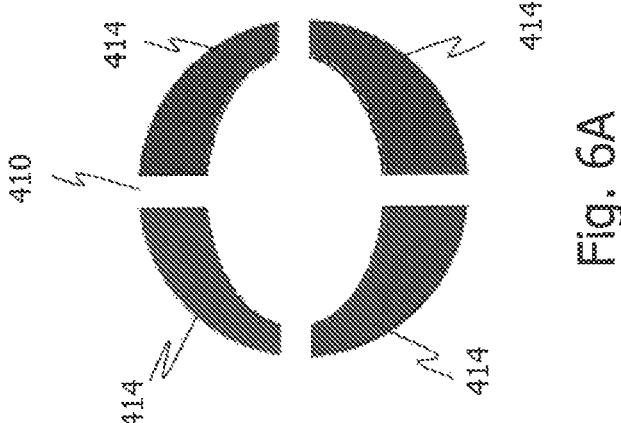

FIGS. 6A to 6C illustrate schematic representations of cross-sections of differently shaped fixation bodies 410. Each of the fixation bodies 410 comprises multiple clamping members 414 extending circumferentially about the longitudinal axis $A_L$. The clamping members 414 are adapted for clamping instrument parts with different cross-sectional shapes. The clamping members 414 shown in FIG. 6A are adapted for clamping an instrument part 210, 220 with an elliptic cross-section. The clamping members 414 shown in FIG. 6B are adapted for clamping an instrument part 210, 220 with a quadratic cross-section. The clamping members 414 shown in FIG. 6C are adapted for clamping an instrument part 210, 220 with a triangular cross-section. The number of the clamping members 414 may be adapted to any suitable number, e.g., 6, 8, 10, 12 or more. Further, the shape of the clamping fingers may be adapted to clamp shapes different from the ones shown in FIGS. 6A to 6C, e.g., arbitrary polygonal shapes.

FIGS. 7A to 7H illustrate schematic representations of alternative fixation devices 400. It is to be noted that the inclinations relative to the longitudinal axis $A_L$ are exaggerated for ease of explanation.

Figures 7A, 7B, 7C:
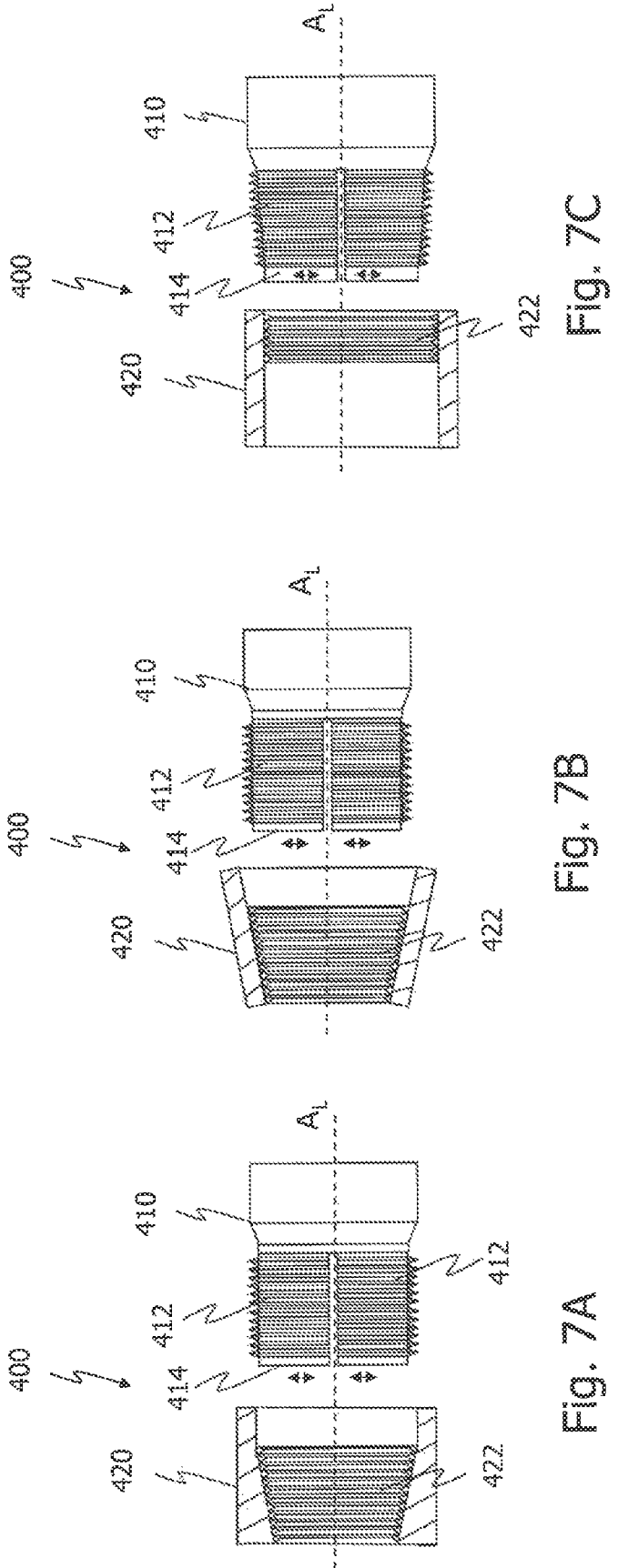
FIGS. 7A-7H illustrate schematic representations of different fixation devices.

The fixation device 400 shown in FIG. 7A comprises an actuation member 420 with an inclined radially inner surface shaped so that only a portion of the inner surface forms a cone. Further, the engagement member 422 (i.e., thread) is located on the cone shaped part. In other embodiments, the engagement member 422 may be located only in the actuation member portion not forming a cone, or it may span all of the inner surface. The fixation body 410 has radially inner and outer surfaces in the region of the clamping members 414 that have a cylindrical configuration.

The actuation member shown in FIG. 7B comprises a cone-shaped actuation member 420. In this variant, the actuation member 420 has inclined radially inner and outer surfaces that are again cone-shaped. The fixation body 410 again has radially inner and outer surfaces in the region of the clamping members 414 that have a cylindrical configuration.

The fixation device 400 shown in FIG. 7C comprises an actuation member 420 with cylindrical radially inner and outer surfaces. In this variant, the clamping members 414 are inclined and have a cone-shape radially outer surface. The clamping members 414 are dimensioned so that a cross-section of the fixation body 410 at the end of the clamping members 414 directed towards the actuation member 420 is smaller than an inner cross section of the cylindrical actuation member 420. The cross-section of the fixation body 410 at the end of the clamping members 414 directed away from the actuation member 420 is larger than the inner cross section of the cylindrical actuation member 420. This variant facilitates fastening of the fastening member 412 to the fastening member 422, i.e., thread engagement.

Figures 7D, 7E:
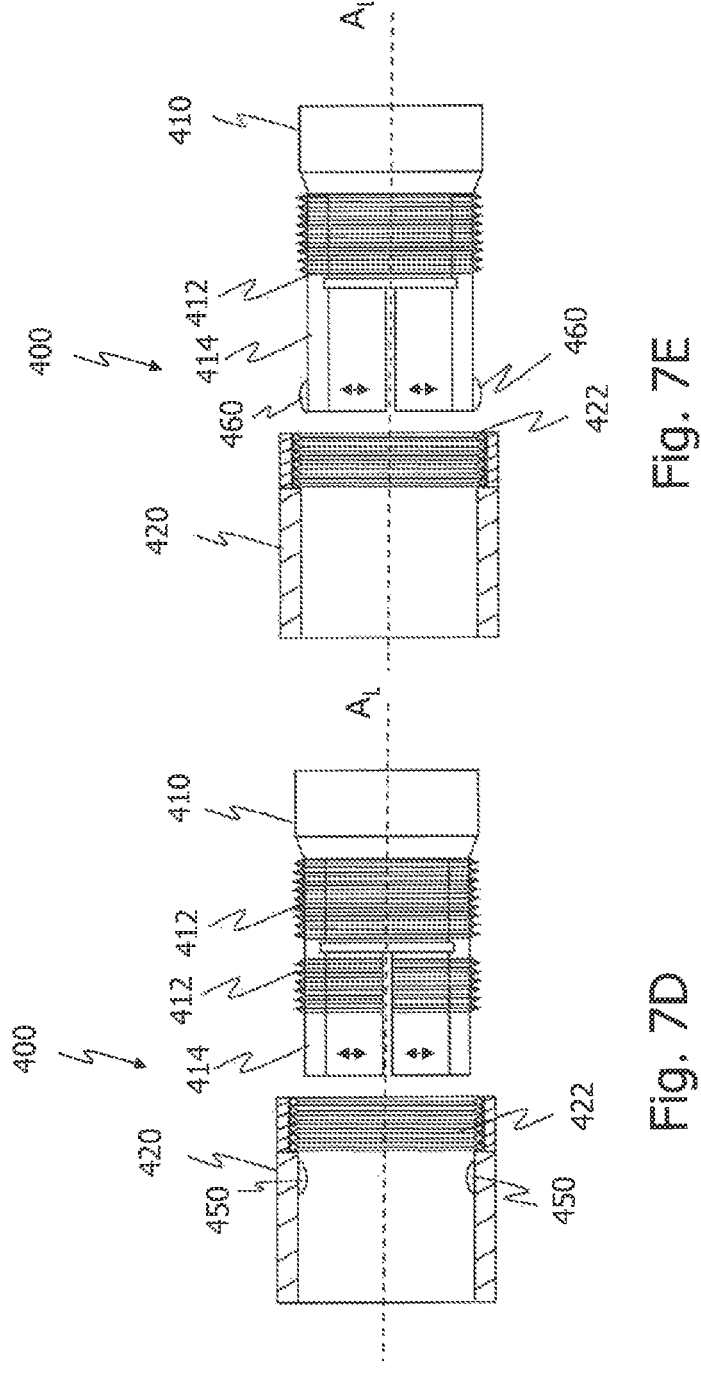

The fixation device 400 shown in FIG. 7D differs from the previously shown variants in that no cone-type or similar inclined surface is formed by any part of the fixation device 400. Instead, the actuation member 420 comprises a protrusion 450 extending from its radially inner surface as a lip circumferentially about and towards the longitudinal axis $A_L$. When the fixation body 410 is received by the actuation device, a force is exerted on the movable clamping members 414 by the protrusion 450, which causes the clamping members 414 to pivot at their end adjacent to the remainder of the fixation body towards the longitudinal axis $A_L$. Depending on the number of clamping members, the protrusion may have a circumferential extension of less than 360°.

The fixation device 400 shown in FIG. 7E comprises a fixation body 410 with movable protrusions 460 located at the respective radially outer surface of the movable clamping members 414 and at the free ends thereof. A force directed towards the longitudinal axis $A_L$ is exerted on the clamping members 414 when the fixation body 410 is received within the actuation member 420 and the protrusions 460 come into engagement with the radially inner surface of the actuation member 420. In some variants, this radially inner surface may be inclined such that the actuation member 420 has a larger inner cross-section at its end facing the fixation body 410.

Figure 7G:
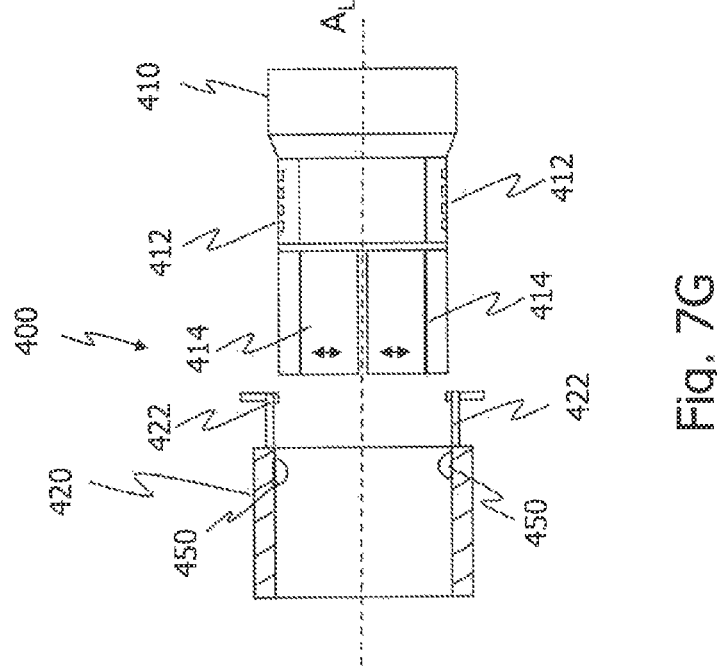
Figure 7F:
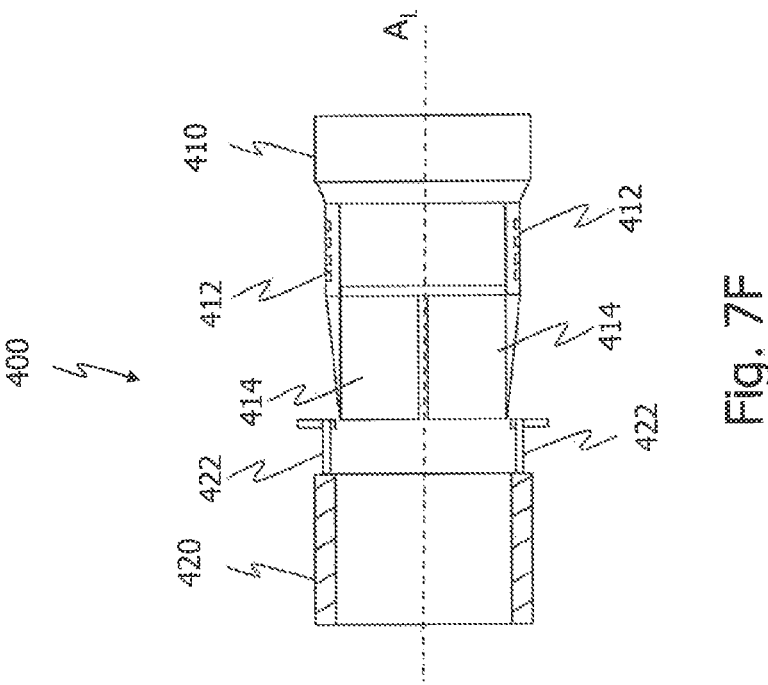

The fixation devices 400 shown in FIGS. 7F and 7G are similar to the fixation devices shown in FIGS. 7C and 7D. The fixation devices 400 shown in FIGS. 7F and 7G differ from the fixation devices shown in FIGS. 7C and 7D in that the fixation devices 400 comprise complementary snap fit elements as fastening members 412, 422 instead of complementary threads. For example, the complementary snap fit elements comprise grooves in a radially outer surface of the fixation body 410 that extend in a circumferential direction and are spaced apart from each other along the longitudinal axis $A_L$. On the actuation member 420, the complementary snap fit elements comprise T-shaped or L-shaped members configured to engage the grooves under a biasing force directed towards the longitudinal axis $A_L$ as the actuation member 420 is pushed onto the fixation body 410.

Figure 7H:
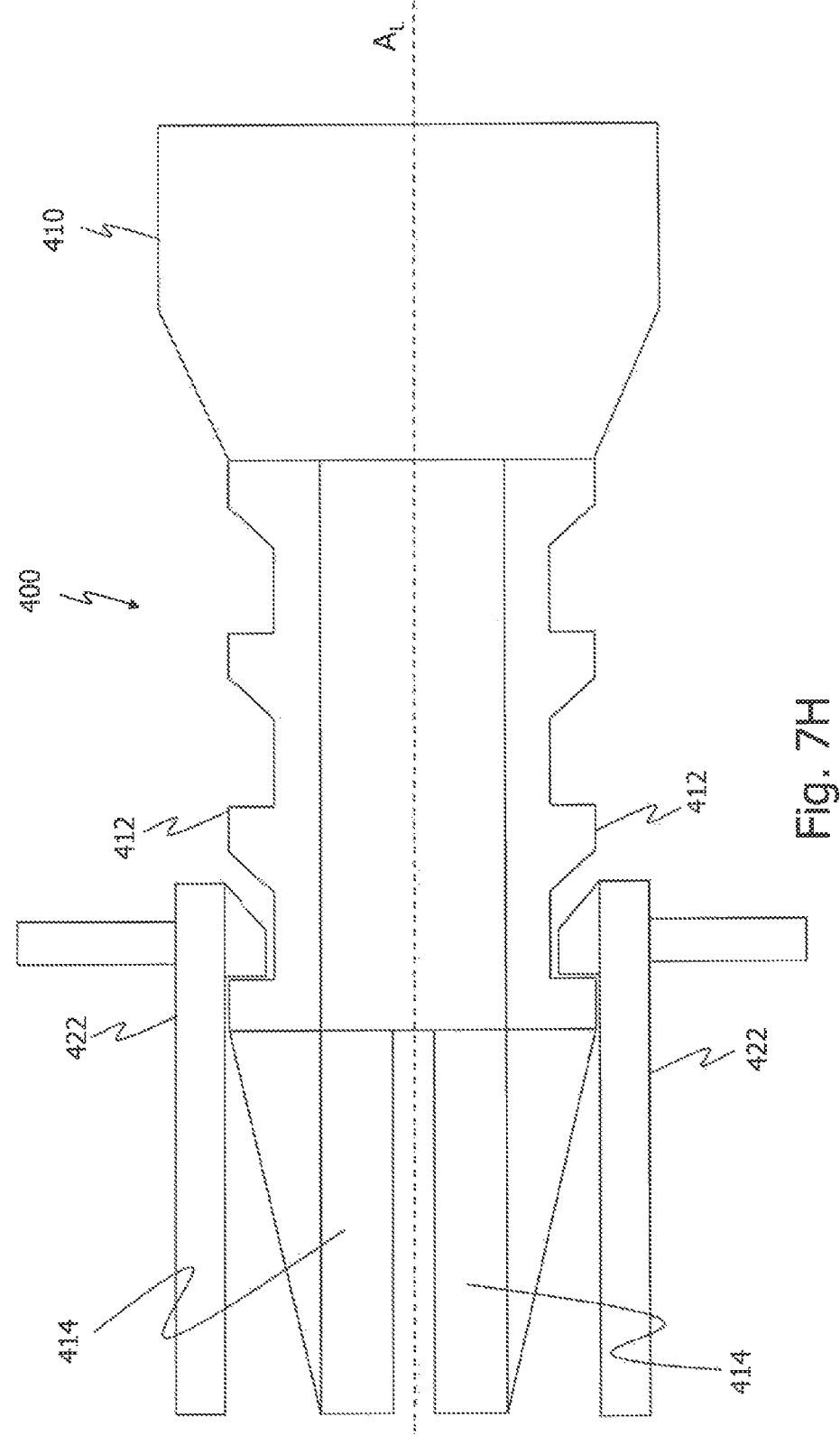

FIG. 7H schematically shows the the complementary snap fit elements 412, 422 in an engaging configuration. The snap fit elements 412, 422 are shaped so that a relative movement between the fixation body 410 and the actuation member 420 along the longitudinal axis $A_L$ is enabled in a first direction, and prevented in a second direction opposite to the first direction. In particular, a relative movement with the fixation body 410 and the actuation member 420 moving further towards each other is enabled. A relative movement with the fixation body 410 and the actuation member 420 moving away from each other is prevented. To enable a relative movement between the fixation body 410 and the actuation member 420 along the longitudinal axis $A_L$ in the second direction, the complementary snap fit elements 412, 422 must be actively disengaged from each other.

While different combinations of the structural elements of the fixation body 410 and the actuation member 420 have been presented above, it is evident that alternative configurations may be provided.

Figure 8:
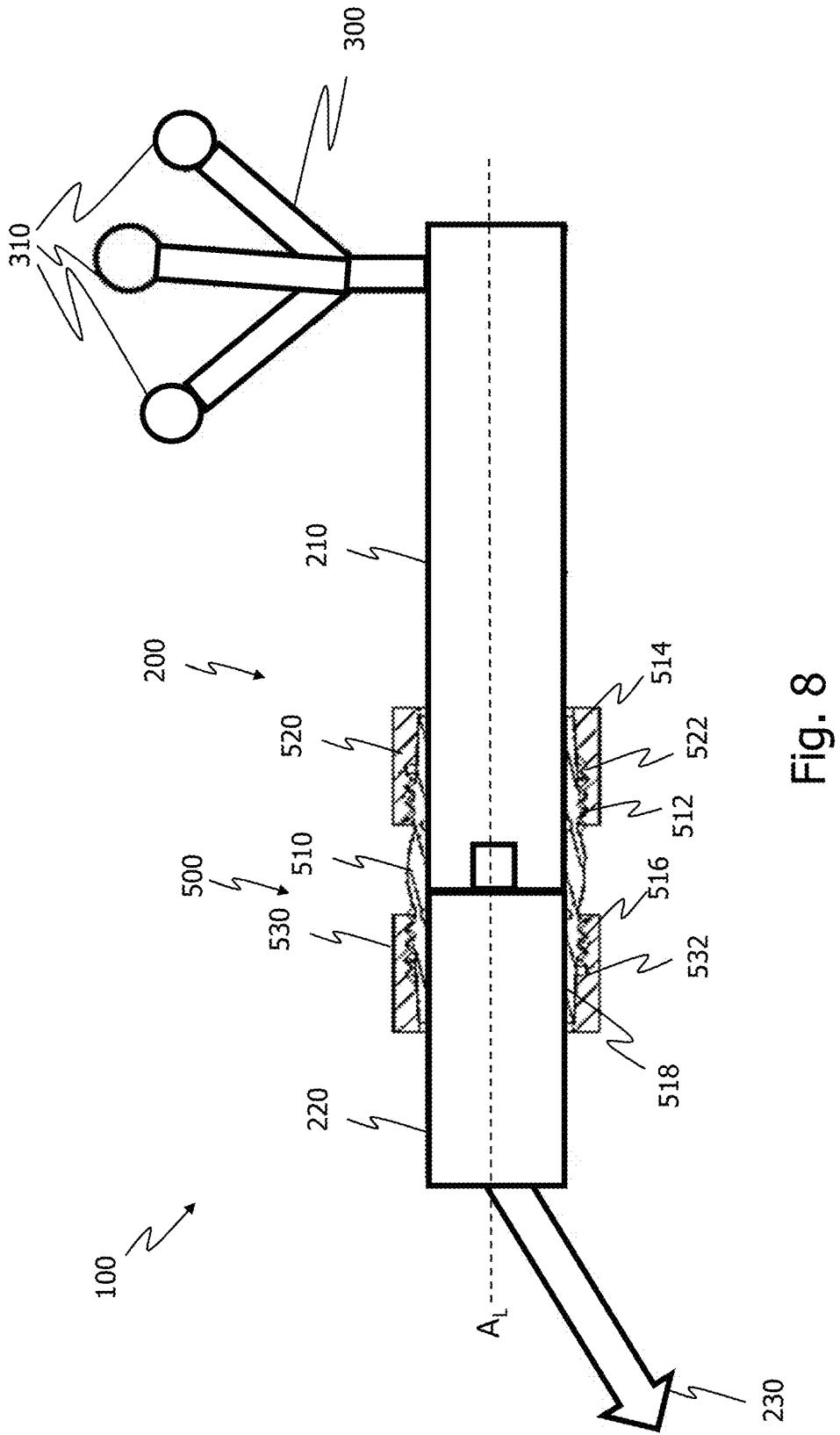
FIG. 8 illustrates a schematic representation of another fixation system comprising a surgical instrument, an alternative fixation device and a tracker.

FIG. 8 illustrates a schematic representation of another embodiment of a fixation system 100 comprising a surgical instrument 200, a fixation device 500 and a tracker 300. The surgical instrument 200 and tracker 300 correspond to the ones shown in FIG. 1.

The fixation device 500 illustrated in FIG. 8 comprises, analogous to the fixation device of FIG. 1, a fixation body 510 with a first fastening member 512 and first movable clamping members 514 at one end thereof. In addition, the fixation body 510 comprises a further fastening member 516 and further movable clamping members 518 at an opposite end.

Moreover, the fixation device 500 comprises a first actuation member 520 with a dedicated fastening member 522 and a second actuation member 530 with another fastening member 532. The fastening member 522 of the first actuation member 520 is configured to engage with the fastening member 512 at one end of the fixation body 510 for fixing the first instrument part 210 to the fixation device 500. The fastening member 532 of the second actuation member 530 is configured to engage with the fastening member 516 at the other end of the fixation body 510 for fixing the second instrument part 220 to the fixation device 500. Therefore, each of the instrument parts 210 and 220 are separately fixed to the fixation device 500.

Figures 9, 10A, 10B:
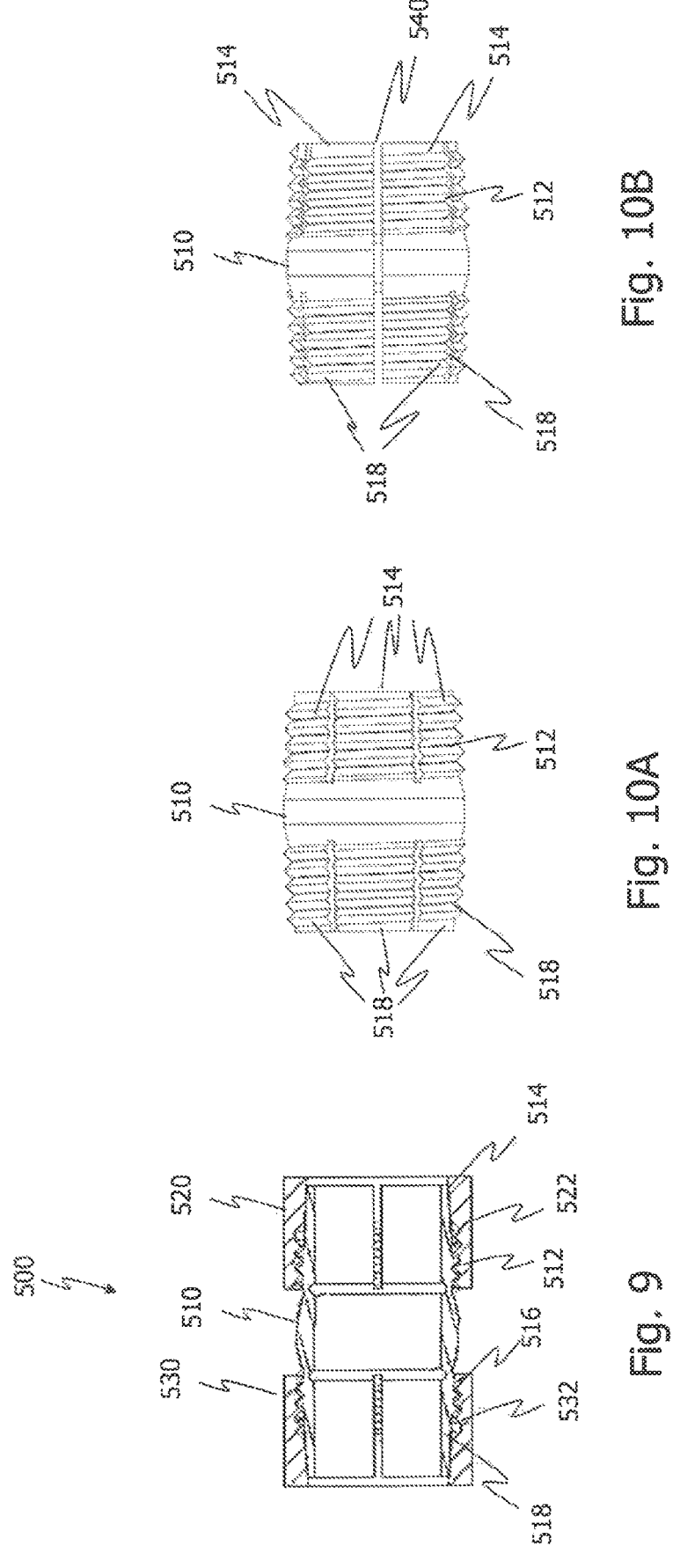
FIG. 9 illustrates a schematic representation of the alternative fixation device shown in FIG. 8.
FIG. 10A illustrates a schematic representation of a fixation body of the alternative fixation device shown in FIG. 9.
FIG. 10B illustrates a schematic representation of another fixation body comprising a slot along a length thereof.

FIG. 9 illustrates a schematic representation of the fixation device 500 shown in FIG. 8. The fixation device 500 comprises two symmetric halves along its longitudinal axis $A_L$. Each halve is constructed analogous to the fixation device 400 shown in FIG. 2. In particular, connecting the fixation bodies 410 of two fixation devices 400 as shown in FIG. 2 such that the movable clamping members 414 are located in opposite directions results in the fixation device 500 shown in FIG. 9.

FIG. 10A illustrates a schematic representation of the fixation body 510 of the fixation device 500. The fastening members 512, 516 are threads located on the opposite clamping members 514, 518.

FIG. 10B illustrates a schematic representation of another fixation body 510 comprising a slot 540 extending along the entire length thereof. Analogous to the slot 430 of the fixation body 410 shown in FIG. 4C, the slot 540 enables adapting the cross-sectional size of the fixation body 510 to the cross-sectional size of the first and second instrument parts 210, 220 to be accommodated by the fixation body 510.

Deviating from what is shown in FIGS. 9 to 10B, the fixation body 510 and the actuation members 520, 530 can have any of the configurations discussed above, for example with reference to FIGS. 4A to 7G.

Figure 11:
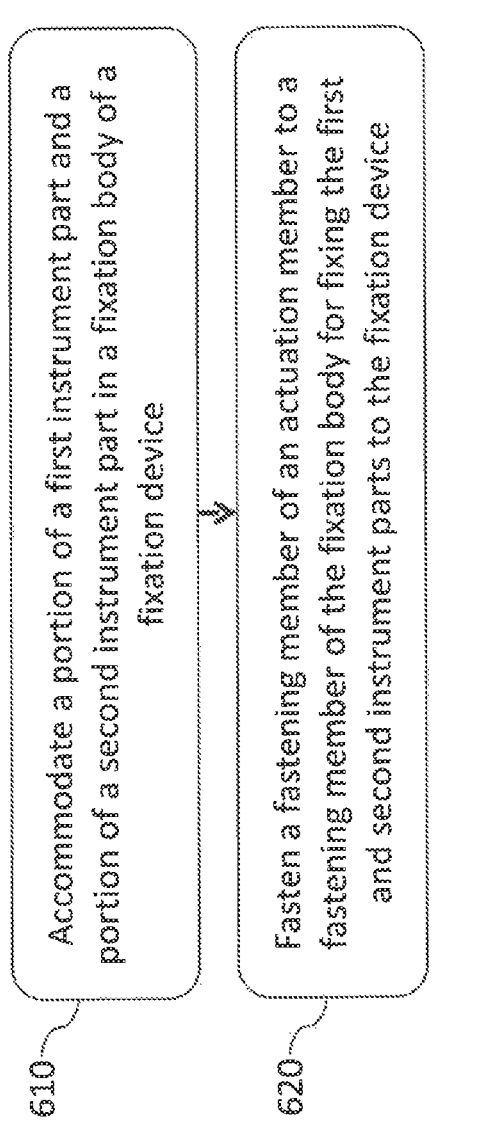
FIG. 11 illustrates a flow diagram of a method for fixing two parts of a surgical instrument to each other using a fixation device as presented herein.

FIG. 11 illustrates a flow diagram 600 of a method for fixing the two parts 210, 220 of the surgical instrument 200 to each other using, for example, the fixation device 400 as described with reference to FIGS. 1 to 7G. Of course, the method could similarly be performed using the fixation device 500 of FIGS. 8 to 10B. The method may be performed by surgical personnel in preparation of a surgical procedure.

A first step 610 comprises accommodating a portion of the first instrument part 210 and a portion of the second instrument part 220 in the fixation body 410 of the fixation device 400.

A second step 620 comprises fastening the fastening member 422 of the actuation member 420 to the complementary fastening member 412 of the fixation body 410 for simultaneously fixing the first instrument part 210 and the second instrument part 220 to the fixation device 400.

In case of using the fixation device 500 as described with reference to FIGS. 8 to 10B, the first step 610 may be analogous as described with reference to the fixation device 400. In method step 620, the two actuation members 520, 530 may separately be fastened, via their respective engagement member 522, 532, to the corresponding engagement member 512, 518 of the fixation body 510.

In a further step not illustrated in FIG. 11, the geometric relationship between the instrument tip 230 and the tracker 300 may be registered using any known registration technique, such as by bringing the instrument tip 230 in abutment with a divot or other structure of a tracked registration device. Once registration has been performed, a surgical procedure involving the surgical instrument 200 may be started, and navigation instructions may be calculated by a navigation system based on the position (and/or orientation) of the tracked surgical instrument 200 and the registered geometric relationship.

It will be appreciated that the surgical instrument 200 could also be part of a surgical robot. In this case, the instrument tip 230 of the instrument part 220 could be, or could be comprised by, an end effector of the surgical robot, and the other instrument part 210 could be comprised by a tracked robotic arm movable in one or more degrees of freedom.

The devices 400 and 500, the systems 100, and the method 600 as described herein in some variants reduce mechanical play between the first and second instrument parts 210, 220. Reducing mechanical play between parts 210, 220 enables reliably using the surgical instrument 200 in conjunction with surgical tracking and navigation techniques and reduces tracking and navigation errors.

The invention claimed is:

1. A fixation device for fixing a first part of a surgical instrument to a second part of the surgical instrument, the fixation device having a longitudinal axis and comprising:

a fixation body configured to accommodate a portion of the first instrument part and a portion of the second instrument part therein, the fixation body comprising a first fastening member and movable first clamping members configured to clampingly engage at least the first instrument part so as to fix at least the first instrument part to the fixation device; and a first actuation member configured to receive at least a portion of the fixation body and comprising a second fastening member configured to engage with the first fastening member, wherein the first actuation member is configured to exert a clamping force on the first clamping members when the second fastening member is in engagement with the first fastening member, wherein the first actuation member comprises cylindrical radially inner and outer surfaces and the first clamping members are inclined and have a cone-shape radially outer surface, wherein the first clamping members are dimensioned so that a cross-section of the fixation body at an end of the first clamping members directed towards the first actuation member is smaller than an inner cross section of the cylindrical first actuation member and that the cross-section of the fixation body at the end of the first clamping members directed away from the first actuation member is larger than the inner cross section of the cylindrical first actuation member.

2. The fixation device of claim 1, wherein at least one of the fixation body and the first actuation member has a structural configuration such that the clamping force is adjustable by a relative movement between the fixation body and the first actuation member along the longitudinal axis.

3. The fixation device of claim 2, wherein the structural configuration comprises a protrusion extending substantially perpendicular to the longitudinal axis.

4. The fixation device of claim 2, wherein the structural configuration comprises a protrusion extending substantially perpendicular to the longitudinal axis.

5. The fixation device according to claim 1, wherein the fixation body has a slot extending along a length thereof, the slot enabling adapting a cross section of the fixation body perpendicular to the length of the fixation body.

6. The fixation device according to claim 5, wherein the slot is a separating slot and the length corresponds to an entire length of the fixation body.

7. The fixation device according to claim 1, wherein the first actuation member is configured as a sleeve.

8. The fixation device according to claim 1, wherein the first clamping members are clamping fingers configured to be deformed towards the longitudinal axis when the clamping force is exerted thereon.

9. The fixation device according to claim 1, wherein the first fastening member and the second fastening member are configured as complementary threads.

10. The fixation device according to claim 1, wherein the fixation body comprises an alignment member configured to align the fixation body with at least one of the first instrument part and the second instrument part in a circumferential direction relative to the longitudinal axis.

11. A method for fixing first and second instrument parts of a surgical instrument to each other using a fixation device having a longitudinal axis, the fixation device comprising:

a fixation body configured to accommodate a portion of the first instrument part and a portion of the second instrument part therein, the fixation body comprising a first fastening member and movable first clamping members configured to clampingly engage at least the first instrument part so as to fix at least the first instrument part to the fixation device; and a first actuation member configured to receive at least a portion of the fixation body and comprising a second fastening member configured to engage with the first fastening member, wherein the first actuation member is configured to exert a clamping force on the first clamping members when the second fastening member is in engagement with the first fastening member, wherein the actuation member comprises cylindrical radially inner and outer surfaces and the clamping members are inclined and have a cone-shape radially outer surface, wherein the first clamping members are dimensioned so that a cross-section of the fixation body at an end of the first clamping members directed towards the first actuation member is smaller than an inner cross section of the cylindrical first actuation member and that the cross-section of the fixation body at the end of the first clamping members directed away from the first actuation member is larger than the inner cross section of the cylindrical first actuation member, wherein the method comprises:

accommodating a portion of the first instrument part and a portion of the second instrument part in the fixation body; and fastening the second fastening member of the first actuation member to the first fastening member of the fixation body for fixing at least the first instrument part to the fixation device.

12. A fixation system comprising:

a surgical instrument having a first instrument part and a second instrument part; and a fixation device for fixing the first instrument part to the second instrument part, the fixation device having a longitudinal axis and comprising:

a fixation body configured to accommodate a portion of the first instrument part and a portion of the second instrument part therein, the fixation body comprising a first fastening member and movable first clamping members configured to clampingly engage at least the first instrument part so as to fix at least the first instrument part to the fixation device; and a first actuation member configured to receive at least a portion of the fixation body and comprising a second fastening member configured to engage with the first fastening member, wherein the first actuation member is configured to exert a clamping force on the first clamping members when the second fastening member is in engagement with the first fastening member, wherein the first actuation member comprises cylindrical radially inner and outer surfaces and the first clamping members are inclined and have a cone-shape radially outer surface, wherein the first clamping members are dimensioned so that a cross-section of the fixation body at an end of the first clamping members directed towards the first actuation member is smaller than an inner cross section of the cylindrical first actuation member and that the cross-section of the fixation body at the end of the first clamping members directed away from the first actuation member is larger than the inner cross section of the cylindrical first actuation member.

13. The fixation system according to claim 12, wherein the first instrument part is configured to transfer mechanical or electrical energy to the second instrument part.

14. The fixation system according to claim 12, wherein the second instrument part comprises a mechanically or electrically operable instrument tip.

15. The fixation system according to claim 12, further comprising a tracker attachable or attached to the first instrument part.

* * * * *